(12) United States Patent
Graf et al.

(10) Patent No.: US 10,684,237 B2
(45) Date of Patent: Jun. 16, 2020

(54) METHOD FOR OPERATING AN X-RAY DEVICE AND ASSOCIATED X-RAY DEVICE

(71) Applicant: Siemens Healthcare GmbH, Erlangen (DE)

(72) Inventors: Alexander Graf, Forchheim (DE); Stefan Hartmann, Eggolsheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 274 days.

(21) Appl. No.: 15/647,586

(22) Filed: Jul. 12, 2017

(65) Prior Publication Data
US 2018/0024080 A1 Jan. 25, 2018

(30) Foreign Application Priority Data
Jul. 21, 2016 (DE) .......... 10 2016 213 379

(51) Int. Cl.
*G01N 23/046* (2018.01)
*A61B 6/00* (2006.01)
*A61B 6/03* (2006.01)

(52) U.S. Cl.
CPC .......... *G01N 23/046* (2013.01); *A61B 6/032* (2013.01); *A61B 6/4266* (2013.01); *A61B 6/54* (2013.01); *G01N 2223/419* (2013.01); *G01N 2223/5015* (2013.01)

(58) Field of Classification Search
CPC .......... G01N 23/046; G01N 2223/419; G01N 2223/5015; A61B 6/54; A61B 6/4266; A61B 6/032
See application file for complete search history.

(56) References Cited

U.S. PATENT DOCUMENTS

| 2005/0169263 | A1* | 8/2005 | Grottel | .......... | H04J 3/247 370/389 |
| 2005/0216236 | A1 | 9/2005 | Such et al. | | |
| 2006/0007766 | A1* | 1/2006 | Krumme | .......... | A61B 6/56 365/202 |
| 2007/0280405 | A1 | 12/2007 | Krumme et al. | | |
| 2010/0299014 | A1* | 11/2010 | Bouvier | .......... | A61B 6/4405 701/25 |
| 2010/0310039 | A1 | 12/2010 | Lindorfer | | |

(Continued)

FOREIGN PATENT DOCUMENTS

CN 1655719 A 8/2005
CN 1781453 A 6/2006
(Continued)

OTHER PUBLICATIONS

Office Action for Chinese Patent Application No. 201710602255.9 dated Feb. 3, 2020 and English translation thereof.

*Primary Examiner* — Christine S. Kim
(74) *Attorney, Agent, or Firm* — Harness, Dickey & Pierce, P.L.C.

(57) ABSTRACT

A method is disclosed for operating an x-ray device, in particular a computed tomograph, including a controller and a number of detector units coupled thereto for signaling purposes. Each of the detectors includes a functional unit and a number of detector elements coupled thereto. In an embodiment of the method, a synchronized clock signal for activating the detector elements is created from a control signal of the controller on the functional unit side.

21 Claims, 1 Drawing Sheet

(56) References Cited

U.S. PATENT DOCUMENTS

2012/0250968 A1* 10/2012 Kappler ................ A61B 6/032
                                                        382/131
2015/0014545 A1   1/2015 Weissler et al.
2018/0123716 A1*  5/2018 Eismann ................ A61B 6/42

FOREIGN PATENT DOCUMENTS

| CN | 1820705 A      | 8/2006  |
|----|----------------|---------|
| CN | 101715318 A    | 5/2010  |
| CN | 102727234 A    | 10/2012 |
| CN | 103634094 A    | 3/2014  |
| CN | 104136939 A    | 11/2014 |
| DE | 102008054128 A1| 10/2007 |

* cited by examiner

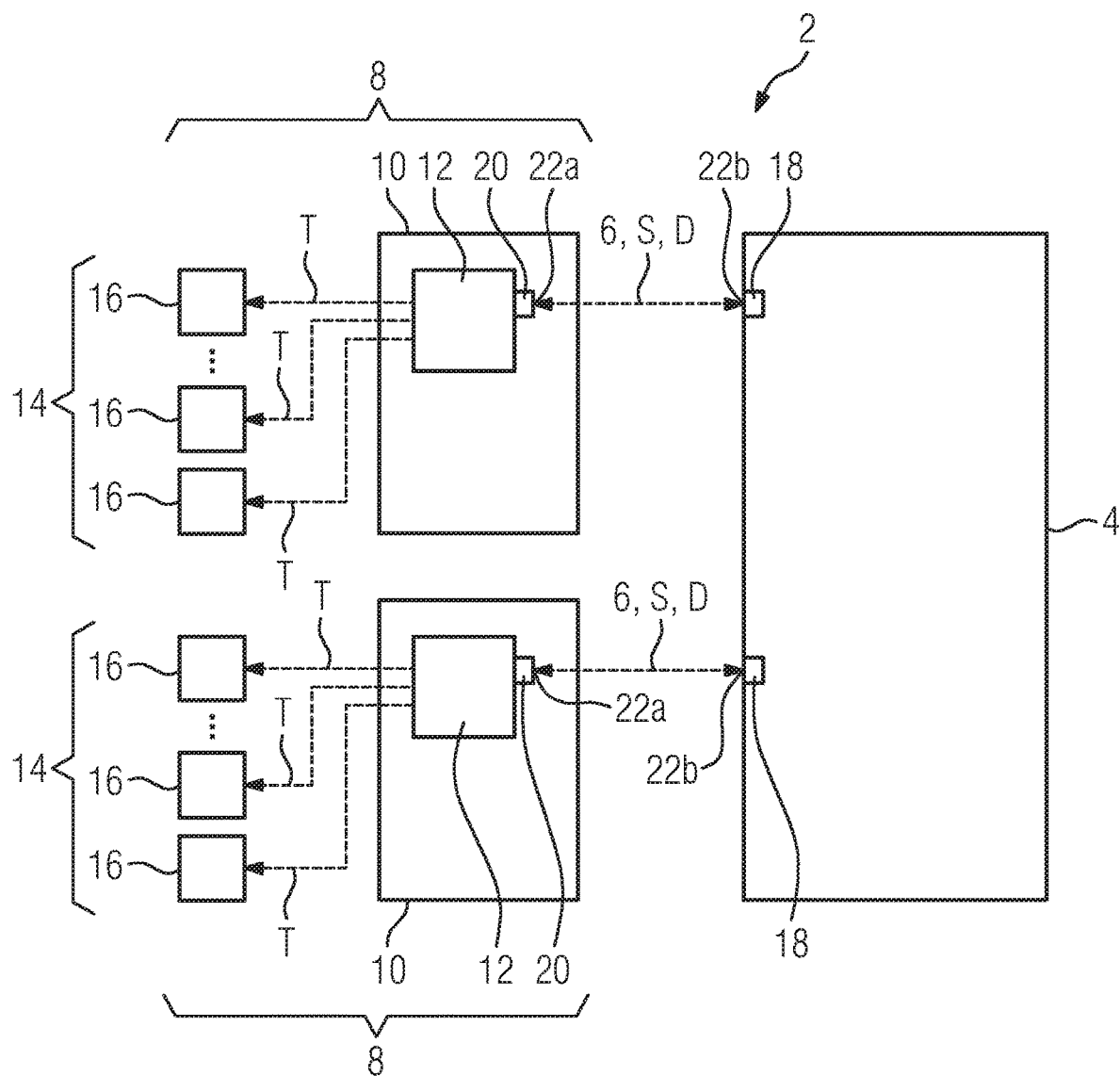

METHOD FOR OPERATING AN X-RAY DEVICE AND ASSOCIATED X-RAY DEVICE

PRIORITY STATEMENT

The present application hereby claims priority under 35 U.S.C. § 119 to German patent application number DE 102016213379.9 filed Jul. 21, 2016, the entire contents of which are hereby incorporated herein by reference.

FIELD

At least one embodiment of the invention generally lies in the field of medical technology, in particular in the field of radiology, and generally relates to a method for operating an x-ray device, in particular a computed tomograph, and also generally relates to an x-ray device suitable for such a method.

BACKGROUND

Nowadays imaging methods are important in medical diagnostics. Modalities, such as for example x-ray devices, make possible recordings from the inside of a patient's body. Computed tomographs as x-ray devices are known, in which, by evaluation of a plurality of individual x-ray recordings, a two-dimensional or three-dimensional sectional representation to show the structures of the body can be created.

For the purposes of x-ray recording such a computed tomograph typically has a number of detector units, with which the radiation of an x-ray source is detected. During the examination the patient is positioned between the x-ray source and the detector units, wherein the different body structures absorb the x-ray radiation to different degrees. The different absorption or the intensity of the x-ray radiation that varies thereby is detected by the detector units and further processed by signaling technology to create a pictorial representation (x-ray image).

The detector units each comprise a plurality of individual detector elements (tiles), which are coupled in signaling technology terms by way of a functional unit to form a common, typically two-dimensional, detector array. The functional units acquire the measurement data and status information of the detector elements and send this for evaluation to a controller as the central control unit of the computed tomograph.

For activation of the detector elements, the controller sends a respective control signal to the functional units, which activate the individually assigned detector elements as a function of the control signal. Before each scan or each x-ray recording or data recording respectively it is therefore necessary for the controller to send corresponding scan parameters to the functional units. The functional units distribute the scan parameters accordingly to the individual detectors, generate offset tables and furthermore insure that the data recording or the x-ray measurement of the detector elements takes place in a synchronized manner. This means that a plurality of checking and/or control signals is needed during the operation of the x-ray device.

As a rule a clock signal is sent from the controller to the functional units for synchronizing the data recording. The functional units here typically have a multiplexer, which distributes the clock signal to a local control unit of the respective functional unit as well as to the individual assigned detector elements.

SUMMARY

The inventors have recognized that, in order to insure that the detector elements are operating synchronously, it is necessary for the multiplexers to have a clock skew that is as small as possible. This means that such multiplexers are comparatively expensive, which is disadvantageously carried across to the manufacturing costs of the x-ray device.

The inventors have further recognized that a plurality of signals, which are to be transmitted during operation between the controller and the functional units, is needed for a reliable control and monitoring as well as evaluation of the detector elements and of the functional units. This means that fast (checking/control) bus lines are needed between the controller and the functional units, so that the configuration and readout of the functional units is effected as quickly as possible.

As a result of the plurality of signals to be transmitted, the inventors have recognized that comparatively complex control interfaces are embodied between the controller and the functional units. The complexity means that that susceptibility to errors is disadvantageously increased. Furthermore these types of interfaces or signal lines are comparatively expensive.

At least one embodiment of the invention specifies an especially suitable method for operating an x-ray device. At least one embodiment of the invention further specifies an x-ray device especially suitable for this method.

At least one embodiment of the invention is directed a method, and at least one embodiment of the invention is directed to an x-ray device. Advantageous embodiments and developments are the subject matter of the respective claims.

At least one embodiment of the inventive method is suitable and configured for operation of an x-ray device, in particular of a computed tomograph. The x-ray device here comprises a controller with a number of detector units connected thereto for signaling purposes. Each detector unit has a functional unit and number of detector elements coupled thereto.

According to at least one embodiment of the method, a synchronized clock signal for activating the detector elements is created from a control signal of the controller on the functional unit side. In other words the functional units create the clock signals themselves and do so locally for activating the assigned detector elements. This does away with expensive multiplexers, which advantageously carries across to the manufacturing costs of the x-ray device.

The inventive x-ray device of at least one embodiment is in particular designed as a computed tomograph. The x-ray device includes a controller with a number of detector units coupled thereto for signaling purposes, each with a functional unit and a number of detector elements coupled thereto. The x-ray device is suitable and configured for carrying out the inventive method. For this purpose each functional unit has an integrated control unit, which creates a synchronized clock signal for activating the detector elements from a control signal of the controller.

The x-ray device of at least one embodiment suitably comprises an x-ray source for generating x-ray radiation. The detector elements here are expediently designed as direct or indirect converting x-ray detectors for the detection of this x-ray radiation. The individual detector elements are preferably arranged in a two-dimensional detector array. The detector elements create an electrical signal as a function of the detected x-ray radiation, which is sent to the respective control unit of the functional units. The control unit forwards these signals as a data signal to the controller, which on the basis of the data signals creates an x-ray recording or an x-ray image.

BRIEF DESCRIPTION OF THE DRAWINGS

An example embodiment of the invention is explained in greater detail below with reference to a drawing. In the drawing the single FIGURE shows a sectional view of an x-ray device with a controller and two detector units connected thereto.

The x-ray device 2 shown in the single FIGURE is preferably embodied as a computed tomograph and in this example embodiment comprises a controller 4 with two detector units 8 connected via a signal line 6 in each case. The detector units 8 each have a functional unit 10 with an integrated control unit 12 as a well as a detector array 14 coupled thereto.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the FIGURES. For example, two FIGURES shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the FIGURE. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method is suitable and configured for operation of an x-ray device, in particular of a computed tomograph. The x-ray device here comprises a controller with a number of detector units connected thereto for signaling purposes. Each detector unit has a functional unit and number of detector elements coupled thereto.

According to at least one embodiment of the method, a synchronized clock signal for activating the detector elements is created from a control signal of the controller on the functional unit side. In other words the functional units create the clock signals themselves and do so locally for activating the assigned detector elements. This does away with expensive multiplexers, which advantageously carries across to the manufacturing costs of the x-ray device.

In a suitable development, the clock signal is created by the functional units through a clock recovery from the control signal. This means that a (data) protocol is used for transmitting the data of the x-ray device, in which a clock recovery (symbol clock synchronization) from the data stream of the received control signals or from the control signals themselves is possible.

The control signals are created by a common (local) clock signal of the controller, through which it is guaranteed that the recovered clock signals of the functional units are in a fixed relationship to one another. Through this a synchronous operation of the functional units and of the detector elements is insured. Furthermore there is no need for an additional signal line for transmission of the clock signal between the functional units and the controller, whereby the setup of the (control) interface between the controller and the detector units is simplified.

In an advantageous embodiment, signals are conveyed bidirectionally between the controller and the respective functional unit. In other words signals from the controller to the functional units (control signals) and signals from the functional units to the controller (data signals) are carried essentially on one common signal line in each case. Through this, the number of signal lines necessary between the controller and the functional unit is further reduced. As a result the reliability and the effort involved in maintaining the x-ray device is improved.

The signals are in particular those control signals that are sent from the controller to the functional units, as well as data signals that are sent from the functional units to the controller. The data signals here comprise detector signals of the individual detector elements, which are sent for imaging evaluation to the controller.

In an expedient embodiment, the signals are transmitted by way of a multiplexing method, in particular by way of a time division multiplexing method (Time Division Multiplex, Time Division Multiple Access), between the functional units and the controller. In the time division multiplexing method, the signals are preferably transmitted in specific time segments (time slots) from the controller to the functional units or respectively from the functional units to the controller. Through this, the data transmission rate between the controller and the functional units is advantageously and easily increased. In other words, it is possible to exchange more data or information (bidirectionally) via a signal line. As a result, the control signals and also the data signals are able to be transmitted via the same physical interface or signal line. This means that separate data and control bus lines are not needed, whereby an especially simple and low-cost structure of the interface is realized.

The inventive x-ray device of at least one embodiment is in particular designed as a computed tomograph. The x-ray device includes a controller with a number of detector units coupled thereto for signaling purposes, each with a functional unit and a number of detector elements coupled thereto. The x-ray device is suitable and configured for carrying out the inventive method. For this purpose each functional unit has an integrated control unit, which creates a synchronized clock signal for activating the detector elements from a control signal of the controller.

The control units are generally configured here—by program and/or circuit technology—for carrying out the method described above. The control units are thus configured in concrete terms to create or to recover a respective clock signal, in particular by way of a clock recovery, from the control signal transferred.

In a preferred form of embodiment, the control units are formed, at least in their core, in each case by a microcontroller with a processor and a data memory, in which the functionality for carrying out at least one embodiment of the inventive method is implemented by programs in the form of operating software (firmware), so that the method—where necessary in interaction with an x-ray device user—is carried out automatically when the operating software is executed in the microcontroller.

Within the framework of at least one embodiment of the invention, the control units can however be formed as an alternative by non-programmable components, for example application-specific integrated circuits (ASICs), in which the functionality for carrying out at least one embodiment of the inventive method is implemented by circuit technology.

The x-ray device of at least one embodiment suitably comprises an x-ray source for generating x-ray radiation. The detector elements here are expediently designed as direct or indirect converting x-ray detectors for the detection of this x-ray radiation. The individual detector elements are preferably arranged in a two-dimensional detector array. The detector elements create an electrical signal as a function of the detected x-ray radiation, which is sent to the respective control unit of the functional units. The control unit forwards these signals as a data signal to the controller, which on the basis of the data signals creates an x-ray recording or an x-ray image.

In an advantageous embodiment, the controller is coupled in each case via a serial signal line to the functional units. The signals are preferably transmitted bidirectionally between the controller and the functional units here. In a suitable embodiment the controller and each control unit of the functional units have a transceiver for this purpose for a bidirectional signal transmission via the respective signal line. Suitably the transceivers are embodied for a multiplexing method, in particular for a time division multiplexing method, for data transmission.

An additional or further aspect of at least one embodiment of the invention makes provision for the signal line to be connected via a plug connector to the controller and/or the functional unit. The plug connector has a plug and a complementary mating connector (socket) in each case here. Through this an especially low-cost interface between the controller and the functional units is realized. In particular a number of functional units or detector units are able to be connected to the controller without any problems.

The x-ray device 2 shown in the single FIGURE is preferably embodied as a computed tomograph and in this example embodiment comprises a controller 4 with two detector units 8 connected via a signal line 6 in each case. The detector units 8 each have a functional unit 10 with an integrated control unit 12 as a well as a detector array 14 coupled thereto.

The detector array 14 has a number of detector elements (tiles) 16, with which x-ray radiation of an x-ray source of the x-ray device 2 can be detected spatially-resolved during operation. The pixel-type detector elements 16 are arranged for this purpose spatially adjacent to one another in relation to the essentially two-dimensional detector array 14.

The detector elements 16 are designed for example as direct-converting or indirect-converting x-ray detectors, which convert the x-ray radiation striking them into an electrical signal in each case. These electrical signals are sent as a measurement or detector signal to the assigned control unit 12. The respective control unit 12 sends a data signal D to the controller 4 as a function of the received signals. The controller 4 evaluates the data signals D and consequently creates an x-ray recording or an x-ray image as a pictorial representation on a display unit not shown in the FIGURE.

The signal line 6 configured as a data and control bus is designed as a bidirectional and serial connection between the controller 4 and the control units 12.

The controller 4 sends a control signal S to the control units 12 during operation, with which the respective functional units 10 as well as the detector arrays 14 are activated. For the purposes of a synchronization of the functional units 10 a protocol is used for the data transmission, which makes possible a clock recovery from the data stream of the control signal S. In other words on the basis of the control signal S the control units 12 create a clock signal T locally in the functional units 10 by a clock recovery.

Since the control signals S of the serial transmission from the controller 4 are created from a same (controller) clock signal, it is insured that the recovered clock signals T of each functional unit 10 are in a fixed (synchronous) relationship to one another. A synchronous operation of the individual detector elements 16 is thereby insured.

The controller 4 and the control units 12, for connection to the signal line 6, are each equipped with a transceiver 18 or 20. The controller 4 sends the control signals S by way of the transceiver 18 via the signal line 6 to the functional unit 10. The control unit 12 receives the control signal S by way of the transceiver 20 and during operation sends the data signal D of the detector array 14 for evaluation to the controller 4.

For the purposes of a data transmission rate that is as high as possible between the controller 4 and the control units 12, the transceivers 18 and 20 are suitable and configured for transmitting the signals S and D by way of a time division multiplex via the signal line 6. Through this an especially simple control interface between the controller 4 and the detector units 8 is realized, which in each case merely has a serial interface for connection of the signal line 6.

For the purposes of an especially simple connection, the signal line 6 is able to be contacted via a plug connector 22a, 22b in each case to the transceivers 18 and 20 of the controller 4 and the functional units 10.

The invention is not restricted to the example embodiment described above. Instead other variants of the invention can also be derived herefrom by the person skilled in the art, without departing from the subject matter of the invention. In particular all individual features described in conjunction with the example embodiment are further also able to be combined with one another in another way, without departing from the subject matter of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for an x-ray device including a controller, a plurality of functional units, each having an integrated control unit, and a plurality of detector units coupled to the controller for signaling purposes, each of the plurality of detector units including a respective functional unit, a respective integrated control unit and a number of detector elements coupled to the respective functional unit, the method comprising:
   creating a synchronized clock signal locally at each respective functional unit, for activating the detector elements coupled to their respective functional unit, based on a clock recovery of a common control signal received from the controller, on a functional unit side of the x-ray device.

2. The method of claim 1, wherein the synchronized clock signal is created by the plurality of the functional units, through clock recovery, from the control signal.

3. The method of claim 2, wherein signals are routed, between the controller and a respective functional unit, bidirectionally.

4. The method of claim 1, wherein signals are routed, between the controller and a respective functional unit, bidirectionally.

5. The method of claim 4, wherein the signals are transmitted by way of a multiplexing method, between the functional units and the controller.

6. The method of claim 5, wherein the multiplexing method is a time division multiplexing method.

7. The method of claim 1, wherein the method is for operating an x-ray device that is a computed tomograph.

8. The method of claim 1, further comprising:
   activating the respective detector elements, via a control unit of each of the respective functional units, using the synchronized clock signal.

9. An x-ray device, comprising:
   a controller; and
   a number of detector units coupled to the controller for signaling purposes, each of the number of detector units including a respective functional unit and a number of detector elements coupled to their respective functional unit, wherein each of the respective functional units includes an integrated control unit configured to locally create a synchronized clock signal for activating the respective detector elements from a control signal received from of the controller.

10. The x-ray device of claim 9, wherein the controller is coupled via a serial signal line to each of the respective the functional units.

11. The x-ray device of claim 10, wherein the controller, and each of the respective control units of the respective functional units, respectively includes a transceiver for a bidirectional signal transmission via a respective signal line.

12. The x-ray device of claim 11, wherein the respective signal lines are connected, via a plug connector, to at least one of the controller and the respective functional unit.

13. The x-ray device of claim 10, wherein the respective signal lines are connected, via a plug connector, to at least one of the controller and the respective functional unit.

14. The x-ray device of claim 9, wherein the x-ray device is a computed tomograph.

15. The x-ray device of claim 9, wherein the detector elements are arranged in a two dimensional detector array.

16. The x-ray device of claim 9, wherein the detector elements are configured to create an electrical signal, as a function of detected x-ray radiation, and send the respective electrical signal to the respective control unit of the respective functional unit.

17. A method for an x-ray device, including a controller and a number of detector units coupled to the controller for signaling purposes, each of the detector units including a respective functional unit, each having an integrated control unit, and a number of detector elements coupled to the respective functional unit, the method comprising:
   creating, via the integrated control unit of each of the respective functional units based on a control signal received from the controller, a synchronized clock signal locally for activating the respective detector elements.

18. The method of claim 17, wherein the synchronized clock signal is created by the plurality of the functional units through a clock recovery, from the control signal of the controller.

19. The method of claim 17, wherein signals are routed, between the controller and each respective functional unit, bidirectionally.

20. The method of claim 17, wherein the signals are transmitted by way of a multiplexing method between the functional units and the controller.

21. The method of claim 17, further comprising:
   activating the respective detector elements, via a control unit of each of the respective functional units, using the synchronized clock signal.

* * * * *